United States Patent [19]

Gladdish, Jr. et al.

[11] Patent Number: 5,255,838
[45] Date of Patent: Oct. 26, 1993

[54] METHOD OF PROVIDING A THREADED BORE IN A PROSTHETIC IMPLANT

[75] Inventors: Bennie W. Gladdish, Jr., Palm Harbor, Fla.; Timothy E. Porter, Warsaw, Ind.

[73] Assignee: Zimmer, Inc., Warsaw, Ind.

[21] Appl. No.: 991,883

[22] Filed: Dec. 17, 1992

[51] Int. Cl.$^5$ .......................................... B23K 31/00
[52] U.S. Cl. .................................. 228/135; 228/125; 623/901
[58] Field of Search ............... 228/135, 125, 140, 175, 228/177, 189, 212; 623/20, 901; 433/174; 606/73

[56] References Cited

U.S. PATENT DOCUMENTS

| | | | |
|---|---|---|---|
| 4,634,444 | 1/1987 | Noiles | 623/20 |
| 4,731,086 | 3/1988 | Whiteside et al. | 623/20 |
| 4,769,039 | 9/1988 | Horber | 623/20 |
| 4,838,891 | 6/1989 | Branemark et al. | 623/20 |
| 4,842,606 | 6/1989 | Kranz et al. | 623/23 |
| 4,846,839 | 7/1989 | Noiles | 623/18 |
| 4,888,021 | 12/1989 | Forte et al. | 623/20 |
| 4,911,721 | 3/1990 | Branemark et al. | 623/20 |
| 4,936,847 | 6/1990 | Manginelli | 623/23 |
| 4,944,757 | 7/1990 | Martinez et al. | 623/20 |
| 4,950,298 | 8/1990 | Gustilo et al. | 623/20 |
| 4,995,883 | 2/1991 | Demane et al. | 623/23 |
| 5,013,313 | 4/1991 | Surer | 606/73 |
| 5,019,103 | 5/1991 | Van Zile et al. | 623/20 |
| 5,047,058 | 9/1991 | Roberts et al. | 623/20 |

FOREIGN PATENT DOCUMENTS

0340919A1 11/1989 European Pat. Off. .

OTHER PUBLICATIONS

"The Genesis TM Total Knee System Design Rationale", Richards Medical Company.
"Insall/Burstein ® II Modular Knee System", Zimmer, Inc., 1989.
"For one Case or Another", There may be a Better Knee Than the GSB Prosthesis.
"Knee Systems, Insall/Burstein II Modular Knee System", Zimmer, Inc. 1991 Catalog.
"P.F.C. ® Modular Total Knee System", Johnson & Johnson, 1991.
"Step Into the Nineties CKS ®", Techmedica.
"The Knee for the Nineties!" Techmedica.
"The Ultimate Measure of Total Knee Arthroplasty . . . Long Term Clinical Performance", Ostenoics Corp. 1990.

*Primary Examiner*—Samuel M. Heinrich
*Attorney, Agent, or Firm*—Todd A. Dawson

[57] ABSTRACT

A method to form a blind bore in an implant wherein a bore is initially drilled through the articular surface of the posterior condyle. The bore is internally threaded and then a plug is welded in place to seal the opening of the bore from the articular surface. The weld bead is polished so that there is no interruption in the articular surface. By drilling and threading the bore from the articular surface, there is no restriction on space, and automated machining equipment can be readily used.

4 Claims, 1 Drawing Sheet

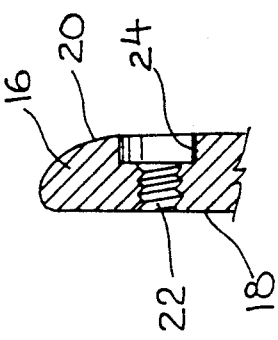
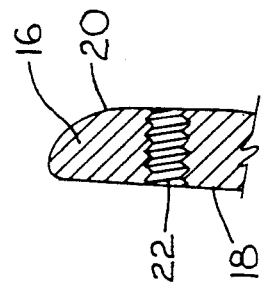
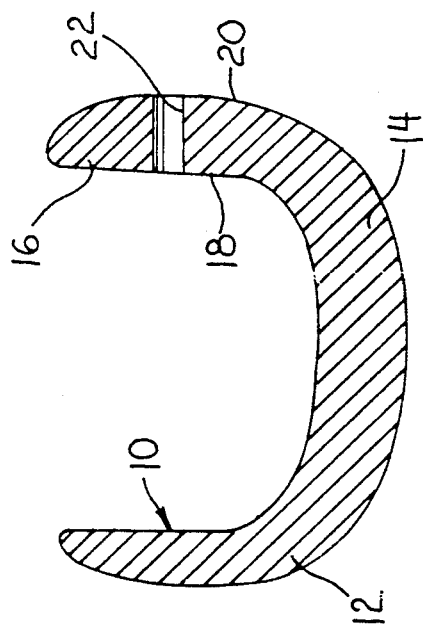
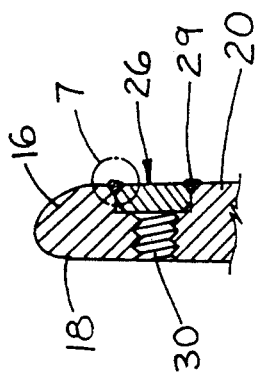
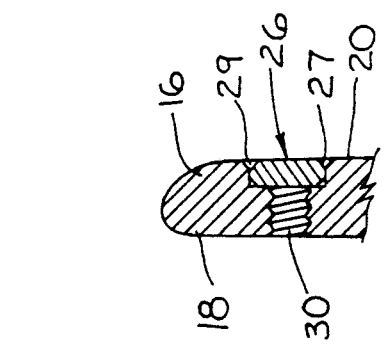
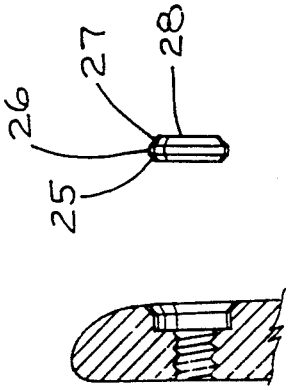
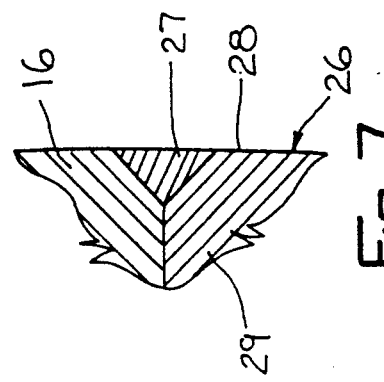

METHOD OF PROVIDING A THREADED BORE IN A PROSTHETIC IMPLANT

FIELD OF THE INVENTION

This invention relates to a method of forming a threaded bore within a prosthetic implant.

BACKGROUND OF THE INVENTION

It is common in a prosthetic implant, specifically in the femoral portion of a knee joint prosthesis, to provide the option to the surgeon of connecting attachments such as augmentation blocks to the implant. A wide variety of attachment mechanisms and methods are known in the industry for connecting such attachments. One method is to provide a bore for accommodation of a peg carried by the augment. The bore can be formed with threads to accommodate a screw securing the augment and implant together.

It is common for a femoral portion of a knee joint prosthesis to include at least the posterior condyle having an interior surface. The general U-shape of the femoral knee prosthesis forms a limited area between the interior surfaces of the condyles and the anterior wall of the prosthesis. Due to this limited space, it is difficult to properly position automated machining equipment to drill a blind bore into the posterior condylar wall. Providing threads within this bore is also very difficult.

SUMMARY OF THE INVENTION

This invention eliminates the difficulties discussed above by providing a method wherein the attachment bore is drilled through the articular surface of the posterior condyle. The bore is internally threaded and then a plug is welded in place to seal the opening of the bore from the articular surface. The weld bead is polished so that there is no interruption in the articular surface. By drilling and threading the bore from the articular surface, there is no restriction on space, and automated machining equipment can be readily used.

Accordingly, it is an object of this invention to provide a method of providing a blind bore within an implant.

Another object of this invention is to provide for a novel method of providing a blind bore in the posterior condyle of a femoral knee joint prosthesis.

Another object of this invention is to provide a method of forming a threaded blind bore in the posterior condylar wall of a femoral knee joint prosthesis by drilling through the condylar articulating surface, threading the bore and back plugging the bore at the articular surface.

Still other objects of the invention will become apparent upon a reading of the following description taken with the accompanying drawings.

BRIEF DESCRIPTION OF THE DRAWINGS

FIG. 1 is a elevational view of a femoral knee joint prosthesis having a bore formed through the posterior condyle in accordance with the method of this invention.

FIG. 2 is a partial elevational view of the posterior condyle of FIG. 1 illustrating a thread formed in the bore of FIG. 1.

FIG. 3 is the partial elevational view of FIG. 2 illustrating the counter bore step of the method of the invention.

FIG. 4 is the partial elevational view of FIG. 3 illustrating the counter bore chamfered.

FIG. 5 is the partial elevational view of FIG. 4 illustrating the chamfered counter bore plugged and welded. The plug used in the method of the invention is illustrated.

FIG. 6 is the partial elevational view of FIG. 5 after the articular surface of the condyle has been polished to remove any interruptions caused by the welding process.

FIG. 7 is an enlarged view of the area circled in FIG. 6 designated by the numeral 7.

DESCRIPTION OF THE PREFERRED METHOD

The preferred method herein described is not intended to be exhaustive or to limit the invention to the precise method disclosed. Rather, it is chosen and described to best explain the invention so that others skilled in the art might utilize its teachings.

Referring now to FIG. 1, a femoral portion of a knee joint prosthesis is illustrated and designated numeral 10. As is common, prosthesis 10 includes an anterior wall 12, distal wall 14 and posterior condyles 16 (only one shown). Posterior condyle 16 includes an interior surface 18 and an articular surface 20. Interior surface 18 is adapted to contact the prepared surface of the femur bone while articular surface 20 is adapted to contact an articular plate. The specific function and geometry of prosthesis 10 is known and is not needed to understand the invention.

To form a threaded blind bore extending from the interior surface of the posterior condyle, a through bore 22 is drilled through the posterior wall of condyle 16 from the articular surface out through the interior surface (See FIG. 1). Next, as illustrated in FIG. 2, a helical thread is formed within the bore 22 by a known method. In the next step in the process, a counter bore 24 is drilled into the articular surface concentric with bore 22 as illustrated in FIG. 3. The counter bore 24 is beveled or chamfered by appropriate milling instrumentation to yield the finished through bore as illustrated in FIG. 4. A plug 26, shaped as illustrated in FIG. 4 to substantially conform to the counter bore, is inserted in the counter bore such that the outer end 28 of the plug is substantially flush with or extending slightly beyond the articular surface of the condyle. As illustrated, plug 26 includes champhered edges 25 and 27. With plug 26 inserted, the junction between champhered edge 27 of the plug and the counter bore 24 forms a V-shaped notch 29 around the plug (see FIG. 5). Plug 26 is mechanically secured to the articular surface of the condyle by welding about the outer perimeter of end 28. Welding the plug into position fills in the V-shaped notch. It should be noted that at this point, the remaining portion of original bore 22 forms a threaded blind bore 30 for the securement of an augmentation block as by a screw. The final step in preparing the implant is to polish the articular surface of the condyle to remove all interruptions in the articular surface of the condyle caused by the welding process.

FIG. 7 illustrates the resulting welded junction between the plug 26, the filled in V-shaped notch 29 and the posterior condyle 16.

It should be understood that the practice of the invention is easily accomplished using computer assisted machining operating from the articular surface of prosthesis. It should be also understood that to ensure accuracy, the prosthesis would be secured in a jig to prevent its movement during the operations.

Finally, it should be understood that the invention is not to be limited to the above forms but may be modified within the scope of the appended claims.

We claim:

1. A method of forming a blind bore within a wall of an orthopaedic implant, the wall including an interior surface and an exterior surface, the method comprising the steps of:
   a. forming a bore through said wall of the orthopaedic implant, the bore extending from the exterior surface to the interior surface of the wall;
   b. forming threads in the bore from the exterior surface to the interior surface; and
   c. providing a plug and plugging said bore at said interior surface and securing said plug to said exterior surface, said plug extending from said exterior surface toward said interior surface within said bore, said plug being spaced from said interior surface.

2. The method of claim 1 further including the steps of:
   d. polishing the exterior surface of said wall and said plug to provide an uninterrupted and smooth exterior surface.

3. The method of claim 1 wherein step a further includes the step of;
   a. forming a counter bore generally concentric with the first mentioned bore and having a larger diameter than the first mentioned bore.

4. A method for the formation of a blind bore in a wall of an orthopaedic joint prosthesis, wherein said wall includes an interior surface and an exterior surface, with said interior surface being in close relationship to a second wall such that a limited space exists between said wall and said second wall, the method including the steps of:
   a. drilling a bore through said wall from said exterior surface toward and through said interior surface;
   b. forming threads in said bore beginning at said exterior surface and extending toward said interior;
   c. forming a counter bore about said bore in said exterior surface, said counter bore extending a partial distance between said exterior wall and said interior wall;
   d. providing a plug substantially conforming to said counter bore;
   e. inserting said plug into said counter bore, said plug being spaced from said interior wall;
   f. securing said plug within said counter bore; and
   g. polishing said exterior surface and an exposed end of said plug such that said exposed end of said plug and exterior surface are flush with one another.

* * * * *

UNITED STATES PATENT AND TRADEMARK OFFICE
CERTIFICATE OF CORRECTION

PATENT NO. : 5,255,838

DATED : October 26, 1993

INVENTOR(S) : Bennie W. Gladdish, Jr. and Timothy E. Porter

It is certified that error appears in the above-identified patent and that said Letters Patent is hereby corrected as shown below:

In Claim 1, column 3, line 19 of the patent, change "interior" to --exterior--.

Signed and Sealed this

Tenth Day of May, 1994

Attest:

BRUCE LEHMAN

*Attesting Officer*     *Commissioner of Patents and Trademarks*